US011826712B2

(12) United States Patent
Schwartz et al.

(10) Patent No.: US 11,826,712 B2
(45) Date of Patent: Nov. 28, 2023

(54) METHOD FOR INCREASING DISSOLUTION OF SOLID CHEMISTRY BLOCKS

(71) Applicant: ECOLAB USA INC., Saint Paul, MN (US)

(72) Inventors: Daniel Ronald Schwartz, Saint Paul, MN (US); Ryan Joseph Drake, Saint Paul, MN (US)

(73) Assignee: ECOLAB USA INC., Saint Paul, MN (US)

(*) Notice: Subject to any disclaimer, the term of this patent is extended or adjusted under 35 U.S.C. 154(b) by 502 days.

(21) Appl. No.: 16/947,783

(22) Filed: Aug. 17, 2020

(65) Prior Publication Data

US 2020/0376447 A1 Dec. 3, 2020

Related U.S. Application Data

(63) Continuation of application No. 16/171,659, filed on Oct. 26, 2018, now Pat. No. 10,773,220.
(Continued)

(51) Int. Cl.
*A61L 2/00* (2006.01)
*B01D 11/02* (2006.01)
(Continued)

(52) U.S. Cl.
CPC .............. *B01F 21/22* (2022.01); *B01F 21/30* (2022.01); *B01F 33/40* (2022.01);
(Continued)

(58) Field of Classification Search
CPC ..... B01F 3/12; B67D 7/08; C02F 1/50; C02F 1/38; C25B 1/26; B63J 4/002
(Continued)

(56) References Cited

U.S. PATENT DOCUMENTS 3,638,833 A * 2/1972 Lucas .................... C02F 1/685 210/123
3,864,090 A 2/1975 Richards
(Continued)

FOREIGN PATENT DOCUMENTS

CN 106687204 A 5/2017
DE 4336339 A1 4/1995
(Continued)

OTHER PUBLICATIONS

Ecolab USA Inc. et al., PCT/US2013/026892 filed Feb. 20, 2013, Notification of Transmittal of The International Search Report and The Written Opinion of The International Searching Authority, or The Declaration, dated Jul. 23, 2013.
(Continued)

*Primary Examiner* — Monzer R Chorbaji
(74) *Attorney, Agent, or Firm* — McKee, Voorhees & Sease, PLC

(57) ABSTRACT

A method and apparatus for obtaining a product chemistry from a solid block is provided. The product is housed within a dispenser, which utilizes a liquid and a gas to erode the block and produce a concentrate solution. The liquid and gas characteristics can be adjusted in the field to achieve a predetermined concentrate level in the solution. The introduction of air into the dispenser saves water, while producing higher concentrate levels.

20 Claims, 3 Drawing Sheets

Related U.S. Application Data

(60) Provisional application No. 62/578,279, filed on Oct. 27, 2017.

(51) Int. Cl.

| | |
|---|---|
| ***A47G 19/00*** | (2006.01) |
| ***B65G 59/00*** | (2006.01) |
| ***B65D 25/08*** | (2006.01) |
| ***C02F 1/76*** | (2023.01) |
| ***B01F 21/20*** | (2022.01) |
| ***B01F 21/00*** | (2022.01) |
| ***B01F 33/40*** | (2022.01) |
| ***B01F 35/22*** | (2022.01) |
| ***B01F 35/71*** | (2022.01) |
| ***B05B 7/24*** | (2006.01) |
| ***B08B 3/08*** | (2006.01) |
| *B01F 101/00* | (2022.01) |

(52) U.S. Cl.
CPC ...... *B01F 35/2202* (2022.01); *B01F 35/7179* (2022.01); *B05B 7/24* (2013.01); *B08B 3/08* (2013.01); *B01F 2101/4505* (2022.01)

(58) Field of Classification Search
USPC ............... 422/28, 261, 292, 300; 220/23.83; 221/92; 206/219; 210/755, 764
See application file for complete search history.

(56) References Cited

U.S. PATENT DOCUMENTS

| | | | | |
|---|---|---|---|---|
| 4,398,669 | A | 8/1983 | Fienhold | |
| 4,790,981 | A | 12/1988 | Mayer et al. | |
| 5,089,127 | A | 2/1992 | Junker et al. | |
| 5,133,381 | A | 7/1992 | Wood et al. | |
| 5,389,344 | A | 2/1995 | Copeland et al. | |
| 5,427,748 | A | 6/1995 | Wiedrich et al. | |
| 5,441,073 | A | 8/1995 | Hoadley | |
| 5,494,644 | A | 2/1996 | Thomas et al. | |
| 5,505,915 | A | 4/1996 | Copeland et al. | |
| 5,810,043 | A | 9/1998 | Grenier | |
| 5,878,781 | A | 3/1999 | Parker | |
| 5,897,770 | A | 4/1999 | Hatch et al. | |
| 5,928,608 | A | 7/1999 | Levesque et al. | |
| 6,423,280 | B1 | 7/2002 | Tarara et al. | |
| 6,531,056 | B2 * | 3/2003 | Hammonds | B01F 35/22142 210/96.1 |
| 7,325,747 | B2 | 2/2008 | Jonte | |
| 7,597,861 | B2 | 10/2009 | Thomas et al. | |
| 7,913,926 | B2 | 3/2011 | Goncze | |
| 7,988,065 | B2 | 8/2011 | Spinelli et al. | |
| 8,945,476 | B2 | 2/2015 | Carroll et al. | |
| 10,773,220 | B2 * | 9/2020 | Schwartz | B08B 3/08 |
| 2002/0195404 | A1 * | 12/2002 | Pickens | B01F 21/22 210/764 |
| 2005/0201200 | A1 | 9/2005 | Fleig | |
| 2005/0244315 | A1 | 11/2005 | Greaves et al. | |
| 2005/0258258 | A1 | 11/2005 | Jonte | |
| 2006/0083668 | A1 | 4/2006 | Thomas et al. | |
| 2006/0231683 | A1 | 10/2006 | Orr | |
| 2007/0253876 | A1 | 11/2007 | Limback et al. | |
| 2012/0260997 | A1 | 10/2012 | Snetting et al. | |
| 2012/0273585 | A1 | 11/2012 | Broome | |

FOREIGN PATENT DOCUMENTS

| | | | |
|---|---|---|---|
| EP | 0225859 | B1 | 6/1987 |
| EP | 1157230 | B1 | 5/2006 |
| EP | 2169511 | A1 | 3/2010 |
| GB | 2467064 | A | 7/2010 |
| JP | 6183497 | U | 6/1986 |
| WO | 2010027625 | A1 | 3/2010 |
| WO | 2019032985 | A1 | 2/2019 |

OTHER PUBLICATIONS

European Patent Office, "Extended European Search Report", issued in connection with International Application PCT/US2013026892, 7 pages, dated Oct. 7, 2015.

Ecolab USA Inc., PCT/US2014/016978 filed Feb. 18, 2014, "The International Search Report and the Written Opinion of the International Searching Authority, or the Declaration", dated Jun. 19, 2014.

Ecolab USA Inc, Application No. 14754429.0/PCT/US2014/016978, "Extended European Search Report" 8 pages, dated Nov. 29, 2016.

Ecolab USA Inc., PCT/US2018/057718 filed Oct. 26, 2018, "The International Search Report and the Written Opinion of the International Searching Authority, or the Declaration", 13 pages, dated Feb. 15, 2019.

* cited by examiner

METHOD FOR INCREASING DISSOLUTION OF SOLID CHEMISTRY BLOCKS

CROSS REFERENCE TO RELATED APPLICATIONS

This application is a Continuation application claiming priority to U.S. Ser. No. 16/171,659, filed on Oct. 26, 2018, which claims priority under 35 U.S.C. § 119 to provisional application U.S. Ser. No. 62/578,279, filed Oct. 27, 2017. The provisional patent application is herein incorporated by reference in its entirety, including without limitation, the specification, claims, and abstract, as well as any figures, tables, appendices, or drawings thereof.

FIELD OF THE INVENTION

The present invention relates generally to a dispenser and method of operation for dispensing a solution from a solid chemistry product. More particularly but not exclusively, the invention relates to a method and apparatus to provide an enhanced control and adjustability in dissolving or eroding the solid product using a combination of an incompressible liquid and compressible gas.

BACKGROUND OF THE INVENTION

Dissolution parameters of a solid product into a liquid solution, such as a liquid detergent used for cleaning and sanitizing, change based on the operating parameters of and inputs to the dissolution process. Spraying liquid onto a solid product to dissolve it into a liquid solution is one technique. With this technique, operating parameters change in part based on characteristics within a dispenser apparatus, such as the distance between the solid product and spray nozzle of the dispenser and change in pressure and temperature of liquid being sprayed onto the solid product. Changes in a nozzle's flow rate, spray pattern, spray angle, and nozzle flow can also affect operating parameters of the dispenser, thereby affecting the chemistry, effectiveness, and efficiency of the concentration of the resulting liquid solution. In addition, dissolution of a solid product by spraying generally requires additional space within the dispenser for the nozzles spray pattern to develop and the basin to collect the dissolved product, which results in a larger dispenser.

Dispensing systems using turbulent flow technology have recently begun utilizing harder solid chemical blocks, which result in low concentration capabilities inside the dispenser. With turbulent flow technology, there are various adjustment options to control the solution concentration that exits the dispenser, such as submersion depth, pluck-to-product height, the number and size of holes in the manifold diffuser, the hole layout, the water temperature, the water pressure, and the like. But there is a limit to these adjustment levels. For example, the holes in the diffuser can only be made to a minimum diameter before fowling with dried chemistry over the life of the dispenser. Also, there is a minimum number of holes required to fully cover the solid chemical blocks' surface to achieve even erosion. The turbulent flow technology platform has been moving toward more challenging block erosions, such as for rinse aids, laundry detergents, and healthcare enzymes. As these blocks have become more and more difficult to dispense, the upper bounds of concentration adjustability become limiting factors.

Therefore, a need exists in the art for a method and apparatus for adjustment of the turbulent flow technology in the field to increase solution concentration and to minimize water usage.

SUMMARY OF THE INVENTION

Accordingly, it is a principle object, feature and/or advantage of the present invention to provide an apparatus and method which overcomes the deficiencies of the prior art.

It is another object, feature and/or advantage of the present invention to provide a turbulent flow technology method and apparatus which utilizes a combination of liquid and gas to erode a solid chemistry block and thereby create a solution with a desired concentration for dispensement.

A further object, feature and/or advantage of the present invention is a provision of a method and apparatus which allows for field adjustments in turbulent flow technology by incorporating pressurized air into the system to displace water for dissolution of the solid chemical block with reduced amounts of water and increased solution concentration levels.

It is still yet a further object, feature, and/or advantage of the present invention to provide a turbulent flow technology method and apparatus that may be used in a wide variety of applications.

It is still yet a further object, feature, and/or advantage of the present invention to provide a turbulent flow technology method and apparatus that is cost effective.

It is still yet a further object, feature, and/or advantage of the present invention to provide a turbulent flow technology method and apparatus that is reliable and durable and has a long usable life.

It is still yet a further object, feature, and/or advantage of the present invention to provide a turbulent flow technology method and apparatus that is easily used and reused.

It is still yet a further object, feature, and/or advantage of the present invention to provide a turbulent flow technology method and apparatus that is easily manufactured, assembled (installed), disassembled (uninstalled), repaired, replaced, stored, transported, and cleaned.

It is still yet a further object, feature, and/or advantage of the present invention to incorporate a turbulent flow technology method and apparatus into a system accomplishing some or all of the previously stated objectives.

The following provides a list of aspects or embodiments disclosed herein and does not limit the overall disclosure. It is contemplated that any of the embodiments disclosed herein can be combined with other embodiments, either in full or partially, as would be understood from reading the disclosure.

According to some aspects of the present disclosure, a dispenser to dispense a solution produced from a solid product comprises a housing having a cavity to hold the solid product, a fluid source combining liquid and gas adjacent the solid block to contact the solid product and thereby erode the solid product to produce the solutions from the eroded solid product and the liquid, and an outlet in the housing for dispensing the solution.

According to some additional aspects of the present disclosure, the dispenser further comprises an air pump within the housing for supplying air to the cavity.

According to some additional aspects of the present disclosure, the dispenser further comprises a pump controller with feedback sensors to provide adjustment to the amount of gas provided.

According to some additional aspects of the present disclosure, the dispenser further comprises a plurality of ports adjacent the cavity, the fluid source being upstream from the ports.

According to some additional aspects of the present disclosure, the dispenser further comprises at least one port for introducing the liquid and gas.

According to some additional aspects of the present disclosure, the dispenser further comprises separate liquid and gas lines connected to the cavity to supply the liquid and the gas to the cavity.

According to some additional aspects of the present disclosure, the dispenser further comprises a fitment splitter creating at least two separate flow paths, each of the flow paths including a flow control to distribute the liquid.

According to some additional aspects of the present disclosure, the dispenser further comprises a manifold diffuse member having manifold diffuse ports and positioned adjacent a fluid source nozzle of the fluid source.

According to some additional aspects of the present disclosure, the dispenser further comprises a product chemistry collector including upstanding walls and a bottom floor comprising the manifold diffuse member.

According to some other aspects of the present disclosure, a method comprises dispensing a solution produced with a dispenser according to any of the aspects described above.

According to some additional aspects of the present disclosure, the method further comprises adjusting characteristics of the liquid and/or the gas prior to introduction through at least one port.

According to some additional aspects of the present disclosure, the characteristics are adjusted in real time based on a density of the solid product, an environmental or climatic condition, a type of the liquid used, a number of solid products being used, or some combination thereof.

According to some additional aspects of the present disclosure, wherein the characteristics comprise pressure, volume, temperature, velocity, turbulence, flow rate, vector and/or impingement.

According to some additional aspects of the present disclosure, the method further comprises adjusting the amount of gas provided.

According to some additional aspects of the present disclosure, the method further comprises distributing the liquid with a flow control.

According to some other aspects of the present disclosure, a method for obtaining a product chemistry from a solid product comprises introducing liquid and gas through at least one port adjacent the solid product, whereby the solid product is eroded to produce a solution from the solid product and the liquid.

According to some additional aspects of the present disclosure, the liquid is introduced near a bottom surface of the solid product via a liquid source nozzle of a liquid source.

According to some additional aspects of the present disclosure, the method further comprises submerging the bottom surface of the solid product in the liquid.

According to some additional aspects of the present disclosure, the method further comprises passing the liquid through manifold diffuse ports of a manifold diffuse member, said manifold diffuse member being positioned adjacent the liquid source nozzle of the liquid source.

According to some additional aspects of the present disclosure, the method further comprises venting the gas away from the solution.

According to some additional aspects of the present disclosure, the method further comprises venting the gas after erosion of the solid product.

According to some additional aspects of the present disclosure, the method further comprises adjusting characteristics of the liquid and/or the gas prior to introduction through the at least one port.

According to some additional aspects of the present disclosure, the characteristics are adjusted in real time based on a density of the solid product, an environmental or climatic condition, a type of the liquid used, a number of solid products being used, or some combination thereof.

According to some additional aspects of the present disclosure, the characteristics comprise pressure, volume, temperature, velocity, turbulence, flow rate, vector and/or impingement.

According to some additional aspects of the present disclosure, the gas and liquid are combined upstream from the ports.

According to some additional aspects of the present disclosure, the gas is air.

According to some additional aspects of the present disclosure, the method further comprises collecting the solution in a product chemistry collector.

According to some other aspects of the present disclosure, a method of dispensing a solution comprises eroding a solid product by impingement of liquid and gas onto the solid product within a cavity in a housing, collecting the eroded solid product and liquid in a reservoir within the housing to produce a solution, and then selectively dispensing the solution from the reservoir.

According to some additional aspects of the present disclosure, the liquid is introduced near a bottom surface of the solid product via a liquid source nozzle of a liquid source.

According to some additional aspects of the present disclosure, the method further comprises submerging the bottom surface of the solid product in the liquid.

According to some additional aspects of the present disclosure, the method further comprises passing the liquid through manifold diffuse ports of a manifold diffuse member, said manifold diffuse member being positioned adjacent the liquid source nozzle of the liquid source.

According to some additional aspects of the present disclosure, the method further comprises venting the gas from the housing as the solid product erodes.

According to some additional aspects of the present disclosure, the method further comprises adjusting characteristics of the liquid and/or the gas to produce a desired concentration for the solution.

According to some additional aspects of the present disclosure, the characteristics are adjusted in real time based on a density of the solid product, an environmental or climatic condition, a type of the liquid used, a number of solid products being used, or some combination thereof.

According to some additional aspects of the present disclosure, the characteristics comprise liquid and gas pressure, volume, temperature, velocity, turbulence, flow rate, vector and impingement.

According to some additional aspects of the present disclosure, the gas is air.

According to some additional aspects of the present disclosure, the method further comprises combing the liquid and gas upstream from the cavity.

According to some additional aspects of the present disclosure, the method further comprises introducing the liquid and gas through at least one port in the cavity.

According to some additional aspects of the present disclosure, the method further comprises supplying the liquid and the gas to the cavity through separate liquid and gas conduits.

These or other objects, features, and advantages of the present invention will be apparent to those skilled in the art after reviewing the following detailed description of the illustrated embodiments, accompanied by the attached drawings.

Figure 1:
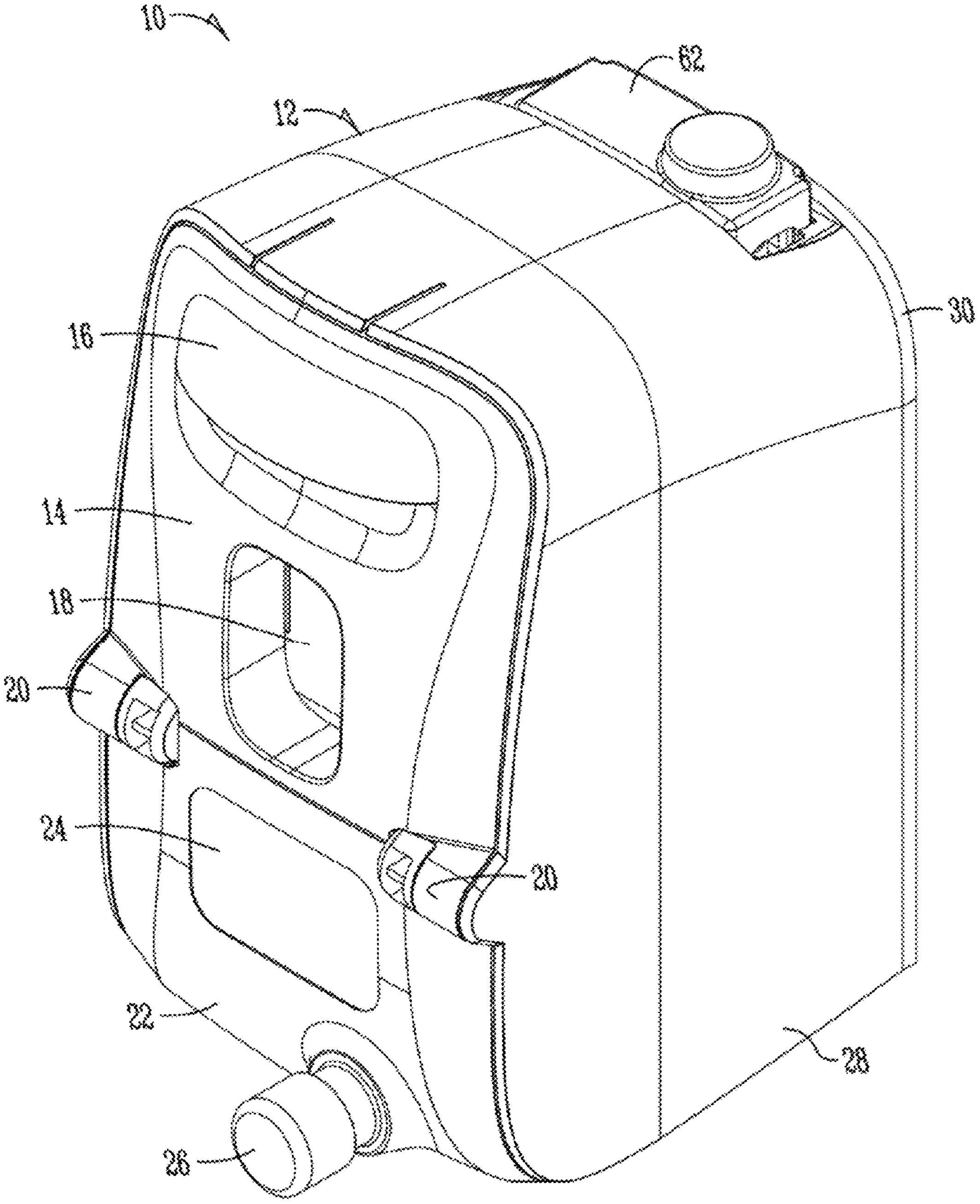
FIG. 1 is a perspective view of one embodiment of a turbulent flow technology dispenser according to the present invention.
Figure 2:
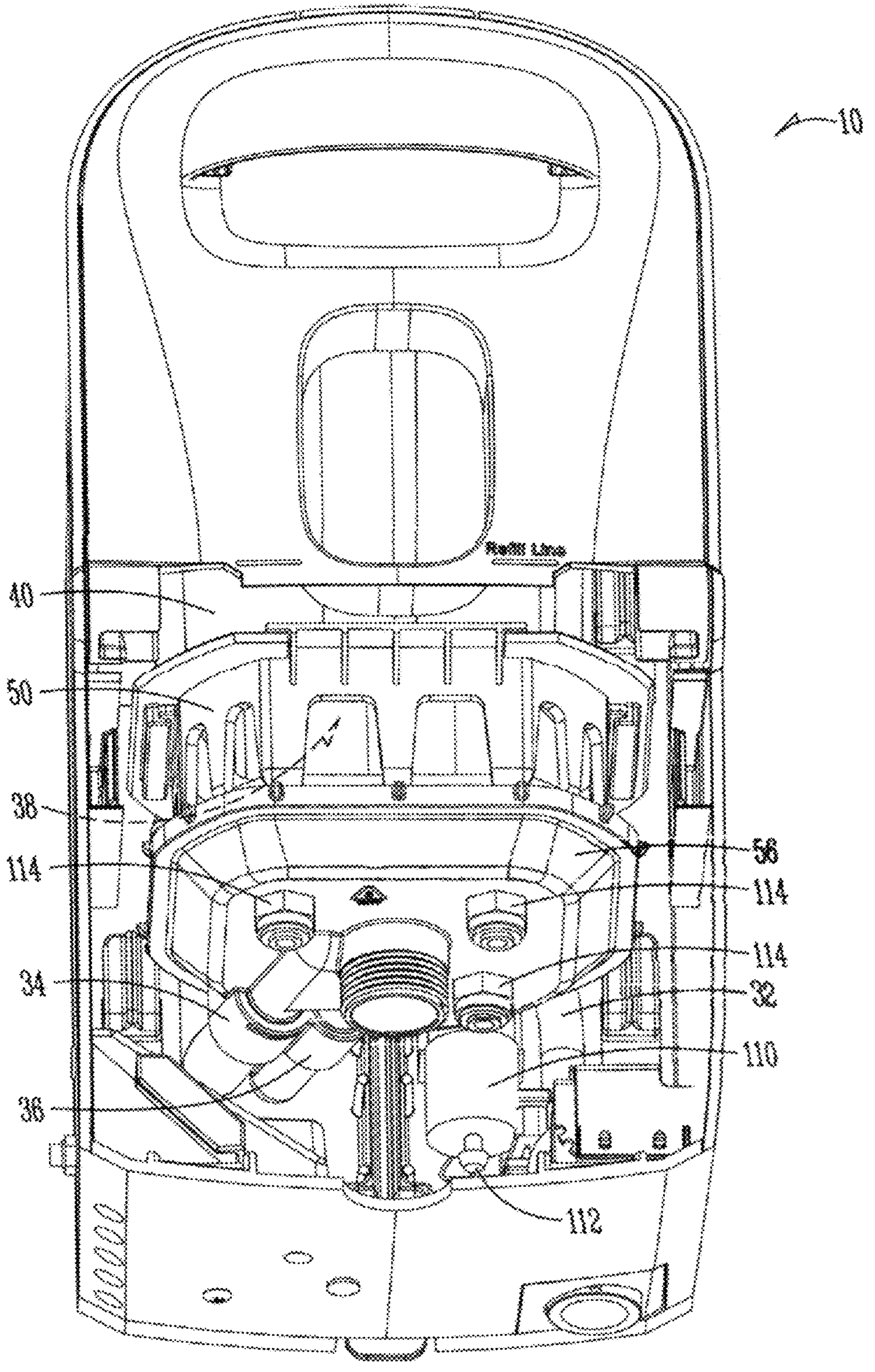
FIG. 2 is another perspective view of the dispenser, with the front fascia removed to show some of the internal components of the dispenser, in accordance with the present invention.
Figure 3:
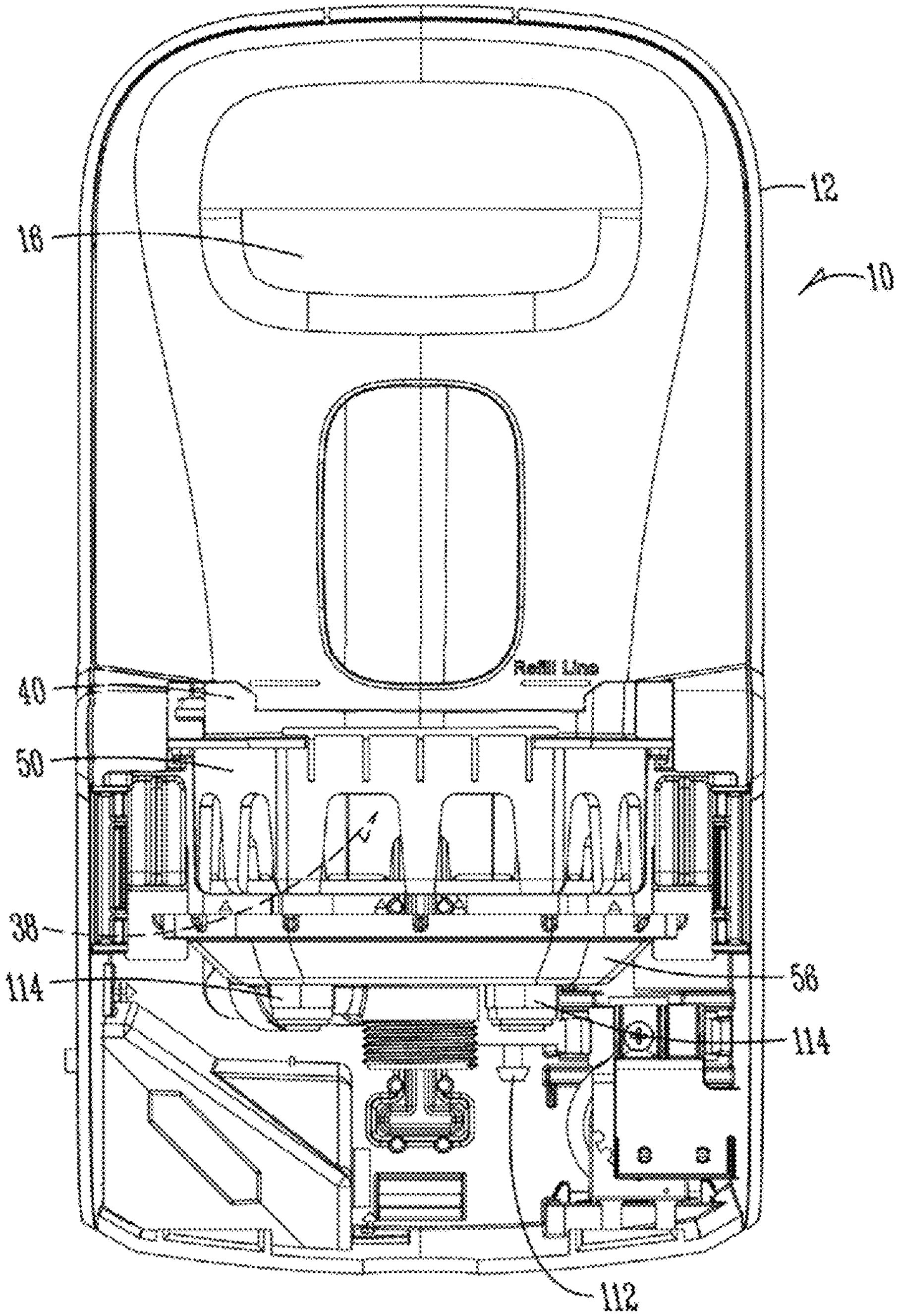
FIG. 3 is a front elevation view, similar to FIG. 2.

Various embodiments of the present disclosure illustrate several ways in which the present invention may be practiced. These embodiments will be described in detail with reference to the drawings, wherein like reference numerals represent like parts throughout the several views. Reference to specific embodiments does not limit the scope of the present disclosure and the drawings represented herein are presented for exemplary purposes.

DETAILED DESCRIPTION OF THE INVENTION

The following definitions and introductory matters are provided to facilitate an understanding of the present invention. Unless defined otherwise, all technical and scientific terms used herein have the same meaning as commonly understood by one of ordinary skill in the art to which embodiments of the present invention pertain.

The terms "a," "an," and "the" include plural referents unless context clearly indicates otherwise. Similarly, the word "or" is intended to include "and" unless context clearly indicate otherwise. The word "or" means any one member of a particular list and also includes any combination of members of that list.

The terms "invention" or "present invention" as used herein are not intended to refer to any single embodiment of the particular invention but encompass all possible embodiments as described in the specification and the claims.

The term "about" as used herein refers to variation in the numerical quantities that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The claims include equivalents to the quantities whether or not modified by the term "about."

The term "configured" describes an apparatus, system, or other structure that is constructed to perform or capable of performing a particular task or to adopt a particular configuration. The term "configured" can be used interchangeably with other similar phrases such as constructed, arranged, adapted, manufactured, and the like.

Terms such as first, second, vertical, horizontal, top, bottom, upper, lower, front, rear, end, sides, concave, convex, and the like, are referenced according to the views presented. These terms are used only for purposes of description and are not limiting. Orientation of an object or a combination of objects may change without departing from the scope of the invention.

The apparatuses, systems, and methods of the present invention may comprise, consist essentially of, or consist of the components of the present invention described herein. The term "consisting essentially of" means that the apparatuses, systems, and methods may include additional components or steps, but only if the additional components or steps do not materially alter the basic and novel characteristics of the claimed apparatuses, systems, and methods.

The following embodiments are described in sufficient detail to enable those skilled in the art to practice the invention however other embodiments may be utilized. Mechanical, procedural, and other changes may be made without departing from the spirit and scope of the invention. Accordingly, the scope of the invention is defined only by the appended claims, along with the full scope of equivalents to which such claims are entitled.

FIG. 1 shows an exemplary embodiment of a dispenser 10 for use with the present invention. However, it should be noted that other types and configurations of dispensers may be used with the invention, and the description and figures of the dispenser 10 are not to be limiting. The dispenser 10 is configured to hold a solid product chemistry that is combined with a liquid, such as water, to create a product chemistry solution. For example, the solid product chemistry may be mixed with the liquid to create a cleaning detergent solution.

According to some embodiments, the dispenser 10 works by having the liquid and gas interact with the solid product to form a product chemistry having a desired concentration for its end use application. The liquid may be introduced to a bottom or other surface of the solid product, as will be disclosed.

Therefore, the dispenser 10 of the invention includes a novel turbulence or flow scheme control that is adjustable either manually or in real time (i.e., automatically) based on a characteristic of either the solid product or another uncontrolled condition, such as an environmental condition. The characteristic may be the density of the solid product, the temperature or pressure of the liquid, the climate (humidity, temperature, pressure, etc.) of the room in which the dispenser or solid product is placed, the type of liquid/fluid used, the number of solid products used, or some combination thereof. The dispenser 10 can be adjusted, such as adjusting a characteristic of the existing flow scheme or turbulence. The adjustments may be made based upon the use of known relationships between the characteristic and the erosion rate of the solid product, as well as the relationship between different types of turbulence and the erosion rate of the solid product.

As mentioned, the turbulence or flow characteristics/scheme can be adjusted based upon known relationships between the characteristic(s) and the dispense rate of the solid chemistry. For example, by understanding the rate change of product dispense per change in degree of liquid temperature change, the turbulence can be adjusted to counteract a temperature change. The concentration is adjusted according to known relationships between the erosion or dispense rate and either the characteristic or the turbulence.

According to the exemplary embodiment, the dispenser 10 of FIG. 1 includes housing 12 comprising a front door 14 having a handle 16 thereon. The door 14 is mounted to the housing in any convenient manner. For example, the front door 14 may be hingeably connected to a front fascia 22 via hinges 20 there between. This allows the front door 14 to be rotated about the hinge 20 to allow access into the housing 12 of the dispenser 10. The front door 14 also includes a window 18 therein to allow an operator to view the solid product housed within the housing 12. Once the housed product has been viewed to erode to a certain extent, the front door 14 can be opened via the handle to allow an operator to replace the solid product with a new un-eroded product.

The front fascia 22 may include a product ID window 24 for placing a product ID label thereon. The product ID window 24 allows an operator to quickly determine the type of product housed within the housing 12 such that replacement thereof is quick and efficient. The ID label may also include other information, such as health risks, manufacturing information, date of last replacement, or the like. The dispenser may be activated in various ways, such as a push button, a switch, or a touch sensitive pad. For example, in one embodiment, a push button 26 is mounted to the front fascia 22 for activating the dispenser 10. The button 26 may be a spring-loaded button such that pressing or depressing of the button activates the dispenser 10 to discharge an amount of product chemistry solution created by the solid product and the liquid. Thus, the button 26 may be preprogrammed to dispense a desired amount per pressing of the button, or may continue to discharge an amount of product chemistry while the button is depressed.

Connected to the front fascia 22 is a rear enclosure 28, which generally covers the top, sides, and rear of the dispenser 10. The rear enclosure 28 may also be removed to access the interior of the dispenser 10. A mounting plate 30 is positioned at the rear of the dispenser 10 and includes means for mounting the dispenser to a wall or other structure. For example, the dispenser 10 may be attached to a wall via screws, hooks, or other hanging means attached to the mounting plate 30.

The components of the housing 12 of the dispenser 10 may be molded plastic or other materials, and the window 18 may be a transparent plastic such as clarified polypropylene or the like. The handle 16 can be connected and disconnected from the front door 14. In addition, a backflow prevention device 62 may be positioned at or within the rear enclosure 28 to prevent backflow of the product chemistry.

A solid product is placed within a cavity 38, which is surrounded by walls 40. The solid product chemistry is placed on a support member 50. The support member 50 may be a grate, a screen, or otherwise include perforations to allow liquid to pass there through A liquid, such as water, is connected to the dispenser 10 via the liquid inlet 32 on the bottom side of the dispenser 10. Activating the dispenser, such as by pressing the button 26, will pass liquid into the dispenser 10 to come in contact with the product chemistry. The liquid is passed through a liquid source 34 via a fitment splitter 36. As shown, the liquid source is a split, two channel liquid source for different flow paths. Each of the paths contains a flow control (not shown) to properly distribute liquid in the intended amounts. This flow control can be changed to alter the turbulence of the liquid coming in contact with the solid product to adjust the turbulence based on the characteristics to maintain the formed product chemistry within an acceptable range of concentration. For example, the liquid may pass through the liquid source 34 and out of the liquid source nozzle 44. The liquid source nozzle 44 is positioned adjacent a manifold diffuse member, which may also be known as a puck member, such that the liquid passing through the liquid nozzle 44 will be passed through manifold diffuse ports of the manifold diffuse member.

Furthermore, the invention contemplates that, while positioned on the support member 50, the product chemistry may be fully submerged, partially submerged, or not submerged at all. The submersion level, or lack thereof, can be dependent upon many factors, including, but not limited to, the chemistry of the product, the desired concentration, the fluid used to erode the chemistry, frequency of use of the dispenser, along with other factors. For example, for normal use with water as the eroding element, it has been shown that it is preferred to have the bottom portion of the product chemistry submerged to aid in controlling the erosion rate of the chemistry. The amount of submersion may depend on the chemistry of the block. For example, for one block chemistry, submersion may be about 0.25-0.75 inch, while a different block chemistry may have about 0.5 to 1.0-inch submersion. This will provide for a more even erosion of the product as it is used, so that there will be less of a chance of an odd amount of product left that must be discarded or otherwise wasted.

The liquid will continue in a generally upwards orientation to come in contact with a portion or portions of the solid product supported by the product grate 50. The mixing of the liquid and the solid product will erode the solid product, which will dissolve portions of the solid product in the liquid to form a product chemistry. This product chemistry will be collected in the product chemistry collector 56, which is generally a cup-shaped member having upstanding walls and bottom floor comprising the manifold diffuse member. The product chemistry will continue to rise in the product chemistry collector 56 until it reaches the level of an overflow port, which is determined by the height of the wall comprising the product chemistry collector 56. A puck or pressurized water vessel sprays water generally upward onto the solid chemistry block. After spraying occurs, the solution cascades over the edges of this component and is collected via a funnel-shaped component for delivery out of the dispenser and into a customer's container.

The liquid source 34 includes a second path, which ends with the diluent nozzle. Therefore, more liquid may be added to the product chemistry in the collection zone, to further dilute the product chemistry to obtain a product chemistry having a concentration within the acceptable range.

Other components of the dispenser 10 include a splash guard positioned generally around the top of the collection zone. The splash guard prevents product chemistry in the collection zone from spilling outside the collection zone.

According to the present invention, the dispenser 10 incorporates a pressurized air into the system to partially displace water used to dissolve the solid chemical block and produce a higher concentration level in the solution. The use of air or other gas, such as nitrogen if inert gas is needed, allows the system to maintain pressure, which is critical for impingement. The air also maintains the spray area for the solid block, while reducing the amount of water volume required to create a solution. The gas or air is also vented out of the system, and thus does not become part of the final chemistry solution. The use of air also eliminates, or at least minimizes, fowling or plugging of the manifold of holes.

The use of air and water helps solve the limitations on solution concentration adjustability, without imposing drastic structural figuration changes in the dispenser 10. The present invention introduces air into the water line to displace liquid volume. Air aids in helping the system maintain spray pressure/volume, with the air leaving the system as soon as it erosion work is complete.

The ratio of liquid to gas varies on a product-by-product basis, depending on the hardness of the solid product or block. Generally, a softer block requires less air than a harder block to obtain the same percentage concentration. Similarly, air pressure also varies, depending on system materials, block hardness, and water parameters. The block hardness can be determined based upon density, moisture content, erodibility, or other test used in industry and which may be known and/or used. Less than 10 psi may be sufficient in some instances. However, it is considered that 0.1 to 100 psi be included as part of the present disclosure for possible pressure ranges.

The dispenser 10 is wired for electrical power inside the housing 12. The dispenser 10 includes an electrical air or gas pump 110. The air pump 110 includes a nipple 112 to which an airline (not shown for clarity) is attached. The airline can be single line, or split into multiple lines, for connection to plumbing points or couplers 114, so as to introduce air into the cavity 38. Thus, liquid, such as water, from the liquid source 34 is combined with gas, such as air, from the pump 110 to effectively dissolve solid chemistry block, and produce the concentrate solution. Upon the activation of the dispenser 10 by pushing the button 26, liquid begins to flow into the system. The pump maybe be activated simultaneously upon pressing the button 26, or alternatively, a delay circuit for the pump 50 can be utilized to ensure the water path is established before introducing air into the system.

By combining air with the liquid to dissolve the solid chemistry block, the solution concentrate can be 2-3 times greater than a turbulent flow dispenser using water alone. Also, the volume of water can be reduced at least 25% due to the addition of air, thus providing costs saving to the operator.

As the gas is provided, at least in part, via a pump 110, which can be connected to a gas source, a pump controller with feedback sensors can provide adjustment to the amount of gas provided. This can allow for the adjustability of the pressure of the gas, the flow rate of the gas, the consistency (pulsing, constant stream, variable flow, random flow, combination, etc.) of the gas stream being input, as well as the on/off of the gas. The pump will provide a near real-time adjustment and operation setting of the gas towards the solid product to aid in controlling the amount of product being eroded with the combination of liquid and gas, and thereby provide a solution concentration within acceptable parameters. The adjustment allows for the control of concentration outputted by the system, and also gives control based upon environment changes (both ambient and based upon dispenser output), erosion rates, and/or other factors that can affect the erosion of the solid product, concentration level of the solution, or other input that may not be controllable in and around the dispensing unit.

The following table shows test results comparing a dispenser according to the present invention run with the auxiliary air both off and on. As shown in the table, the net result is an average of approximately 2× concentration improvement with the use of gas verses no gas. The air pressure being used can correlate or correspond with a water pressure or temperature, such as increasing or decreasing to account for a predetermined threshold of temperature or pressure, or could be independent such that it is included based upon a concentration desired or tested.

TABLE 1

| | Water Inlet Conditions | | | Solution Results | |
|---|---|---|---|---|---|
| Chemistry Type | Temp (° F.) | Press (psi) | Aux. Air On/Off | Grams/ Gallon | % Increase |
| All Purpose Cleaner | 110 | 20 | OFF | 2.29 | |
| All Purpose Cleaner | 125 | 40 | OFF | 2.97 | |
| All Purpose Cleaner | 140 | 60 | OFF | 4.18 | |
| All Purpose Cleaner | 110 | 20 | ON | 3.22 | 40.6% |
| All Purpose Cleaner | 125 | 40 | ON | 4.62 | 55.6% |
| All Purpose Cleaner | 140 | 60 | ON | 6.13 | 46.7% |
| Sanitizer | 110 | 20 | OFF | 2.13 | |
| Sanitizer | 125 | 40 | OFF | 2.58 | |
| Sanitizer | 140 | 60 | OFF | 3.60 | |
| Sanitizer | 110 | 20 | ON | 3.41 | 60.1% |
| Sanitizer | 125 | 40 | ON | 3.82 | 48.1% |
| Sanitizer | 140 | 60 | ON | NO DATA | |

The dispenser 10 according to the aspects of the present disclosure may also include components such as an intelligent control and communication components. Examples of such intelligent control units may be tablets, telephones, handheld devices, laptops, user displays, or generally any other computing device capable of allowing input, providing options, and showing output of electronic functions. Still further examples include a microprocessor, a microcontroller, or another suitable programmable device) and a memory. The controller also can include other components and can be implemented partially or entirely on a semiconductor (e.g., a field-programmable gate array ("FPGA")) chip, such as a chip developed through a register transfer level ("RTL") design process.

The memory includes, in some embodiments, a program storage area and a data storage area. The program storage area and the data storage area can include combinations of different types of memory, such as read-only memory ("ROM", an example of non-volatile memory, meaning it does not lose data when it is not connected to a power source), random access memory ("RAM", an example of volatile memory, meaning it will lose its data when not connected to a power source) Some examples of volatile memory include static RAM ("SRAM"), dynamic RAM ("DRAM"), synchronous DRAM ("SDRAM"), etc. Examples of non-volatile memory include electrically erasable programmable read only memory ("EEPROM"), flash memory, a hard disk, an SD card, etc. In some embodiments, the processing unit, such as a processor, a microprocessor, or a microcontroller, is connected to the memory and executes software instructions that are capable of being stored in a RAM of the memory (e.g., during execution), a ROM of the memory (e.g., on a generally permanent basis), or another non-transitory computer readable medium such as another memory or a disc.

A communications module can be included with the dispenser and can be configured to connect to and communicate with another controller, such as a computer, tablet, server, or other computing device. This could allow the dispenser to provide data or other information (e.g., warnings, status, notices, etc.) associated with the dispenser to a remote location of the additional controller to allow the real-time information and stored information for the dispenser. The information could be used to determine issues, forecast, or otherwise track information related to the dispenser. The communication could also be in the form of inputs such that the communication could include a command to the dispenser from a remote location.

In some embodiments, the dispenser includes a first communications module for communicating with a secondary device (other dispenser or remote controller), and/or a second communications module for communicating with a central location (server, computer, or other master controller). For sake of simplicity, the term "communications module" herein applies to one or more communications modules individually or collectively operable to communicate with both the mobile reader and the central location.

The communications module communicates with the central location through the network. In some embodiments, the network is, by way of example only, a wide area network ("WAN") (e.g., a global positioning system ("GPS"), a TCP/IP based network, a cellular network, such as, for example, a Global System for Mobile Communications ("GSM") network, a General Packet Radio Service ("GPRS") network, a Code Division Multiple Access ("CDMA") network, an Evolution-Data Optimized ("EV-DO") network, an Enhanced Data Rates for GSM Evolution ("EDGE") network, a 3GSM network, a 4GSM network, a Digital Enhanced Cordless Telecommunications ("DECT") network, a Digital AMPS ("IS-136/TDMA") network, or an Integrated Digital Enhanced Network ("iDEN") network, etc.), although other network types are possible and contemplated herein. In certain embodiments, the network is a GSM or other WAM which is operable to allow communication between the communications module and the central location during moments of low-quality connections, such as but not limited to when the cleaning machine is near a window.

In some embodiments, the network is, by way of example only, a wide area network ("WAN") such as a TCP/IP based network or a cellular network, a local area network ("LAN"), a neighborhood area network ("NAN"), a home area network ("HAN"), or a personal area network ("PAN") employing any of a variety of communications protocols, such as Wi-Fi, Bluetooth, ZigBee, near field communication ("NFC"), etc., although other types of networks are possible and are contemplated herein. The network typically allows communication between the communications module and the central location during moments of low-quality connections. Communications through the network can be protected using one or more encryption techniques, such as those techniques provided in the IEEE 802.1 standard for port-based network security, pre-shared key, Extensible Authentication Protocol ("EAP"), Wired Equivalent Privacy ("WEP"), Temporal Key Integrity Protocol ("TKIP"), Wi-Fi Protected Access ("WPA"), and the like.

The connections between the communications module and the network are wireless to enable freedom of movement and operation of the mobile cleaning machine without being physically tethered to a computer or other external processing device to facilitate such communications. Although such a modality of communications is preferred for at least this reason, it is contemplated that the connections between the communications module and the network can instead be a wired connection (e.g., a docking station for the communications module, a communications cable releasably connecting the communications module and a computer or other external processing device, or other communications interface hardware), or a combination of wireless and wired connections. Similarly, the connections between the controller and the network or the network communications module are wired connections, wireless connections, or a combination of wireless and wired connections in any of the forms just described. In some embodiments, the controller or communications module includes one or more communications ports (e.g., Ethernet, serial advanced technology attachment ("SATA"), universal serial bus ("USB"), integrated drive electronics ("IDE"), etc.) for transferring, receiving, or storing data. The central location can include a centrally located computer, a network of computers, or one or more centrally located servers. The central location can be adapted to store, interpret, and communicate data from one or more dispensers 10, and can also interpret the data and communicate the interpreted data to a user.

Thus, the combination of an incompressible liquid and a compressible gas to uniformly dissolve or erode the solid chemistry block provides advantages which cannot be achieved in the prior art.

From the foregoing, it can be seen that the present invention accomplishes at least all of the stated objectives.

LIST OF REFERENCE NUMERALS

The following list of reference numerals is provided to facilitate an understanding and examination of the present disclosure and is not exhaustive. Provided it is possible to do so, elements identified by a numeral may be replaced or used in combination with any elements identified by a separate numeral. Additionally, numerals are not limited to the descriptors provided herein and include equivalent structures and other objects possessing the same function.

10 dispenser
12 housing
14 door
16 handle
18 window
20 hinges
22 front fascia
24 product ID window
26 button
28 rear enclosure
30 mounting plate
32 liquid inlet
34 liquid source
36 fitment splitter
38 cavity
40 walls
44 liquid source nozzle
50 pump
56 product chemistry collector
62 backflow prevention device
110 pump
112 nipple
114 couplers The present disclosure is not to be limited to the particular embodiments described herein. The following claims set forth a number of the embodiments of the present disclosure with greater particularity.

What is claimed is:

1. A dispenser comprising:

a housing having a cavity to hold a solid product;

a fluid source supplying liquid;

a gas source supplying gas;

wherein the liquid and the gas are combined adjacent the solid product to contact the solid product and thereby erode the solid product so as to produce a solution from the eroded solid product and the liquid, wherein the liquid continues in a generally upwards direction and/or orientation until the liquid comes in contact with a submerged portion of the solid product that is supported by a product grate or until the liquid rises to at least one overflow port;

a cup-shaped member having upstanding walls and a bottom floor to collect the solution wherein said cup-shaped member is housed entirely within said housing, and wherein the overflow port is located at a height of the upstanding walls; and a pump operatively connected to the gas source to control the amount of gas supplied.

2. The dispenser of claim 1, further comprising a pump controller operatively connected to the pump.

3. The dispenser of claim 2, wherein the pump controller comprises feedback sensor to provide adjustment to the amount of gas supplied.

4. The dispenser of claim 3, wherein the pump controller further controls the adjustability of one or more of:

a. the pressure of the gas;

b. the flow rate of the gas;

c. the consistency of the gas; and/or d. the on/off of the gas.

5. The dispenser of claim 3, wherein the pump controller provides a near real-time adjustment and operation setting of the supplied gas.

6. The dispenser of claim 1, further comprising a manifold diffuse member causing turbulence in the liquid located between the solid product and the fluid source.

7. The dispenser of claim 1, further comprising a plurality of ports adjacent the cavity, the fluid source being upstream from the ports.

8. The dispenser of claim 1, further comprising at least one port for introducing the liquid and gas.

9. The dispenser of claim 1, further comprising separate liquid and gas lines connected to the cavity to supply the liquid and the gas to the cavity.

10. The dispenser of claim 1, further comprising an outlet in the housing for dispensing the solution towards an end use application.

11. A method of dispensing a solution comprising:

combining gas with a liquid at a solid product to conserve an amount of the liquid needed to (a) maintain pressure and (b) produce a solution;

eroding a solid product supported by a product grate by impingement of the liquid and the gas onto the solid product within a cavity in a housing, wherein the liquid continues in a generally upwards direction and/or orientation until the liquid comes in contact with a submerged portion of the solid product or until the liquid rises to at least one overflow port;

controlling the amount of gas supplied to the combination with a controller;

collecting the eroded solid product and liquid in a reservoir, said reservoir being defined by a cup-shaped member having upstanding walls and a bottom floor and being located within the housing, wherein said cup-shaped member is housed entirely within said housing, and wherein the overflow port is located at a height of the upstanding walls, to produce a solution; and then selectively dispensing the solution from the reservoir.

12. The method of claim 11, further comprising sensing, via a sensor, the amount of gas supplied.

13. The method of claim 12, where the controller comprises a pump controller operatively connected to the pump.

14. The method of claim 13, wherein the pump controller controls the adjustability of one or more of:

a. the pressure of the gas;

b. the flow rate of the gas;

c. the consistency of the gas; and/or d. the on/off of the gas.

15. The method of claim 11, wherein the step of controlling the amount of gas supplied comprises controlling the adjustability of one or more of:

a. the pressure of the gas;

b. the flow rate of the gas;

c. the consistency of the gas; and/or d. the on/off of the gas.

16. The method of claim 11, further comprising adjusting characteristics of the liquid and/or the gas to produce a desired concentration for the solution.

17. The method of claim 16, wherein the characteristics comprise liquid and gas pressure, volume, temperature, velocity, turbulence, flow rate, vector and impingement.

18. A dispenser, comprising:

a housing having a cavity to hold a solid product;

a fluid source supplying liquid;

a gas source supplying gas;

wherein the liquid and the gas are combined adjacent the solid product to contact the solid product and thereby erode the solid product so as to produce a solution from the eroded solid product and the liquid, wherein the liquid continues in a generally upwards direction and/or orientation until the liquid comes in contact with a submerged portion of the solid product that is supported by a product grate or until the liquid rises to at least one overflow port;

a cup-shaped member having upstanding walls and a bottom floor to collect the solution wherein said cup-shaped member is housed entirely within said housing, and wherein the overflow port is located at a height of the upstanding walls; and a controller operatively connected to the gas source to control the amount of gas supplied.

19. The dispenser of claim 18, wherein the controller is connected to a gas pump and a sensor to control the amount of gas supplied.

20. The dispenser of claim 19, wherein the controller provides a near real-time adjustment and operation setting of the supplied gas.

* * * * *